United States Patent
Yoshida et al.

(10) Patent No.: US 12,417,571 B2
(45) Date of Patent: Sep. 16, 2025

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Masashi Yoshida, Nasushiobara (JP); Yasunori Ohshima, Yaita (JP); Tomohiro Kawasaki, Otawara (JP); Takeshi Ezumi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 84 days.

(21) Appl. No.: 18/062,782

(22) Filed: Dec. 7, 2022

(65) Prior Publication Data

US 2023/0186539 A1     Jun. 15, 2023

(30) Foreign Application Priority Data

Dec. 9, 2021    (JP) ................................ 2021-200420

(51) Int. Cl.
| | |
|---|---|
| *G06T 11/60* | (2006.01) |
| *G16H 40/63* | (2018.01) |
| *A61B 5/00* | (2006.01) |
| *A61B 6/46* | (2024.01) |
| *A61B 8/00* | (2006.01) |
| *G06F 3/0481* | (2022.01) |

(52) U.S. Cl.
CPC ............ *G06T 11/60* (2013.01); *G16H 40/63* (2018.01); *A61B 5/7425* (2013.01); *A61B 6/463* (2013.01); *A61B 6/464* (2013.01); *A61B 8/463* (2013.01); *A61B 8/464* (2013.01); *G06F 3/0481* (2013.01); *G06F 2203/04803* (2013.01)

(58) Field of Classification Search
CPC ....... G06T 11/60; G16H 40/63; A61B 5/7425; A61B 6/463; A61B 8/463; G06F 2203/04803
See application file for complete search history.

(56) References Cited

U.S. PATENT DOCUMENTS

| | | | | |
|---|---|---|---|---|
| 8,316,294 | B2 * | 11/2012 | Bay ........................ | A61B 6/566 |
| | | | | 382/128 |
| 11,137,887 | B1 * | 10/2021 | Garibaldi ............... | G16H 40/20 |
| 2004/0109008 | A1 * | 6/2004 | Sako ....................... | G06T 11/60 |
| | | | | 345/629 |

(Continued)

FOREIGN PATENT DOCUMENTS

JP     2007-328678 A     12/2007

*Primary Examiner* — Patrick F Riegler
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry is configured to record, when a layout of a display area is changed at a first step included in a clinical workflow, layout change information that indicates a changed content, determine, when the layout of the display area is changed at the first step, whether to change a layout of a display area set in advance for a second step that is any step after the first step, based on the layout change information, and change the layout at the second step based on a result of determination.

10 Claims, 7 Drawing Sheets

(56) References Cited

U.S. PATENT DOCUMENTS

| | | | |
|---|---|---|---|
| 2005/0100136 A1* | 5/2005 | Kawatsu | H04N 1/407 |
| | | | 378/207 |
| 2007/0214409 A1* | 9/2007 | Miyata | G06F 3/1208 |
| | | | 358/1.15 |
| 2007/0276809 A1* | 11/2007 | Yoshida | G06F 16/34 |
| | | | 707/E17.093 |
| 2008/0008401 A1* | 1/2008 | Zhu | G16H 40/63 |
| | | | 382/294 |
| 2009/0094513 A1* | 4/2009 | Bay | A61B 6/566 |
| | | | 382/128 |
| 2013/0215146 A1* | 8/2013 | Kusakabe | G06T 11/60 |
| | | | 345/619 |
| 2013/0262988 A1* | 10/2013 | Nakagawa | G06F 40/106 |
| | | | 715/243 |
| 2015/0091778 A1* | 4/2015 | Day | G16Z 99/00 |
| | | | 345/1.3 |
| 2016/0048635 A1* | 2/2016 | Warner | G16H 30/00 |
| | | | 715/704 |
| 2017/0031646 A1* | 2/2017 | Imai | G06F 3/1454 |
| 2018/0364879 A1* | 12/2018 | Adam | G06F 3/0481 |
| 2020/0167918 A1* | 5/2020 | Ando | A61B 6/465 |
| 2021/0181932 A1* | 6/2021 | Han | A61B 5/746 |
| 2022/0291818 A1* | 9/2022 | Lee | G06F 3/04845 |

* cited by examiner

| USER | YEARS OF EXPERIENCE | DEPARTMENT | PROFES-SION |
|---|---|---|---|
| USER A | 5 YEARS | INTERNAL MEDICINE | DOCTOR |
| USER B | 7 YEARS | SURGERY | NURSE |
| USER C | 10 YEARS | RADIOLOGY | TECHNICIAN |
| ⋮ | ⋮ | ⋮ | ⋮ |

FIG.4

| STEP | DISPLAY-SUGGESTED INFORMATION | DEGREE OF IMPORTANCE |
|---|---|---|
| STEP A | INFORMATION A | 0.4 |
| | INFORMATION B | 0.1 |
| | INFORMATION C | 0.4 |
| | ⋮ | ⋮ |
| STEP B | INFORMATION A | 0.35 |
| | INFORMATION B | 0.1 |
| | INFORMATION C | 0.35 |
| | ⋮ | ⋮ |
| STEP C | INFORMATION A | 0.1 |
| | INFORMATION B | 0.35 |
| | INFORMATION C | 0.35 |
| | ⋮ | ⋮ |
| ⋮ | ⋮ | ⋮ |

FIG.5

| VIEW | DISPLAYABLE INFORMATION | DEGREE OF IMPORTANCE |
|---|---|---|
| VIEW A | INFORMATION A | 0.3 |
| | INFORMATION B | 0.3 |
| | INFORMATION C | 0.4 |
| | ⋮ | ⋮ |
| VIEW B | INFORMATION A | 0.5 |
| | INFORMATION B | 0.0 |
| | INFORMATION C | 0.5 |
| | ⋮ | ⋮ |
| VIEW C | INFORMATION A | 0.0 |
| | INFORMATION B | 0.0 |
| | INFORMATION C | 1.0 |
| | ⋮ | ⋮ |
| ⋮ | ⋮ | ⋮ |

| DISEASE | MONITORING INFORMATION | DEGREE OF IMPORTANCE |
|---|---|---|
| DISEASE A | INFORMATION J | 0.45 |
| | INFORMATION K | 0.45 |
| | INFORMATION L | 0.1 |
| DISEASE B | INFORMATION L | 0.7 |
| ⋮ | ⋮ | ⋮ |

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2021-200420, filed on Dec. 9, 2021; the entire contents of which are incorporated herein by reference.

FIELD

Embodiments described herein relate generally to a medical information processing apparatus and a medical information processing method.

BACKGROUND

One problem to be solved by embodiments disclosed in the present specification and the drawings is to reduce trouble in layout change. Note that problems to be solved by the embodiments disclosed in the present specification and the drawings are not limited to the above problem. Problems corresponding to respective effects obtained by respective components in the embodiments described later may be regarded as other problems.

BRIEF DESCRIPTION OF THE DRAWINGS

FIG. 4 is a diagram illustrating an example of a data configuration of a step database;

FIG. 5 is a diagram illustrating an example of a data configuration of a view database;

DETAILED DESCRIPTION

Figure 1:
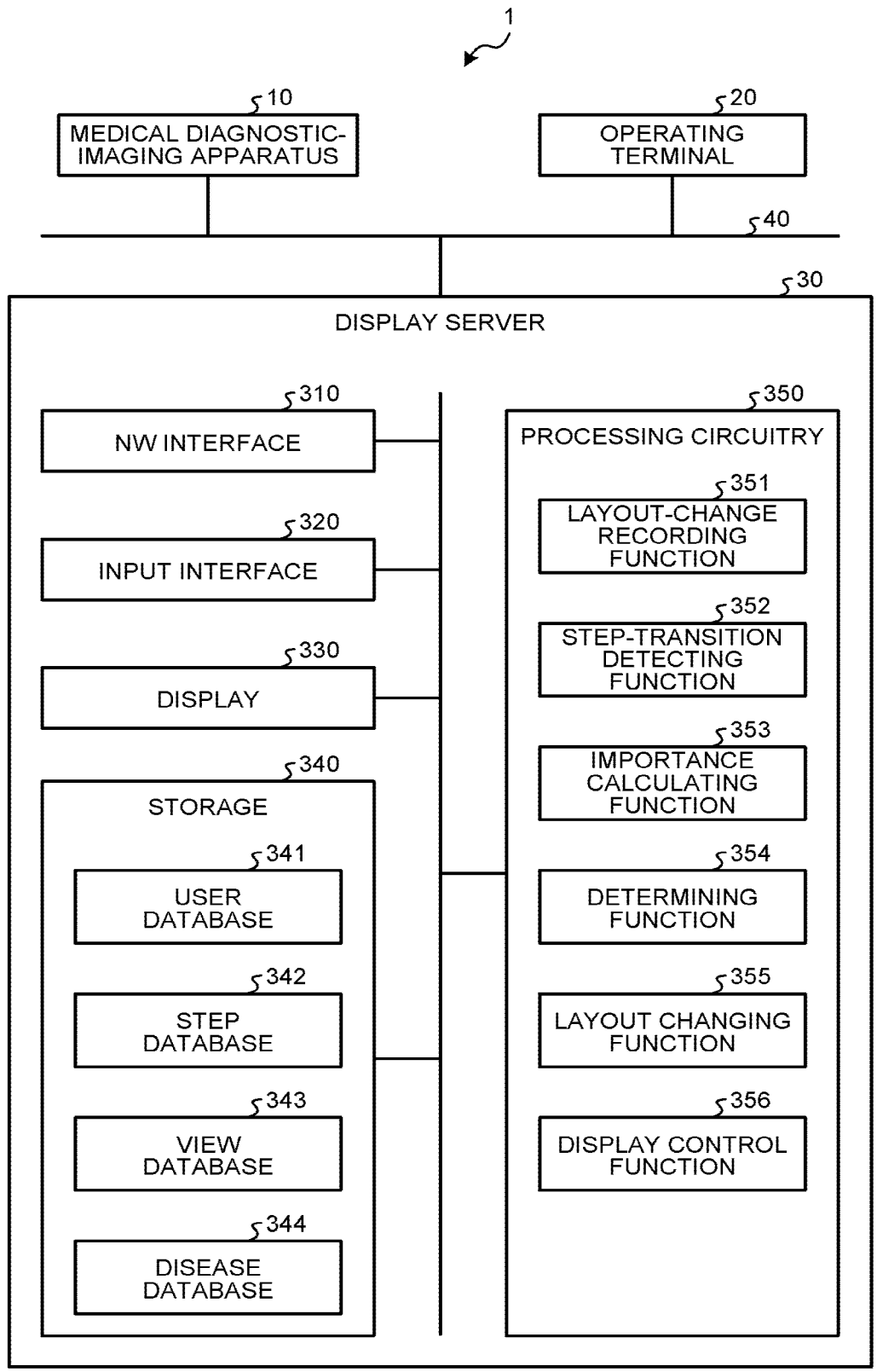
FIG. 1 is a block diagram illustrating an example of a configuration of a medical information-display system according to a first embodiment.

Hereinafter, a medical information processing apparatus and a medical information processing method relating to the present embodiment will be explained, referring to the drawings. In the following embodiments, components having a same reference symbol perform similar actions, and duplicated explanation thereof is omitted as appropriate.

First Embodiment

FIG. 1 is a block diagram illustrating an example of a configuration of a medical information-display system 1 according to a first embodiment. The medical information-display system 1 includes a medical diagnostic-imaging apparatus 10, an operating terminal 20, and a display server 30. Moreover, respective systems and respective devices included in the medical information-display system 1 are connected to one another through a network 40 so that mutual communication is possible. The configuration illustrated in FIG. 1 is one example, and the number of the respective systems and the respective devices may be arbitrarily changed. Moreover, a device not illustrated in FIG. 1 may be connected to the network 40.

The medical diagnostic-imaging apparatus 10 is an apparatus that captures an image to examine a subject. The medical diagnostic-imaging apparatus 10 is, for example, an x-ray diagnostic apparatus, an X-ray computed tomography (CT) apparatus, a magnetic resonance imaging apparatus, a nuclear medicine diagnostic apparatus, an ultrasonic diagnostic apparatus, and the like.

The operating terminal 20 is a terminal that displays various kinds of screens in a clinical workflow, or accepts operations. For example, the operating terminal 20 is implemented by a computer device, such as a personal computer and a tablet terminal.

The display server 30 controls display of a screen in a layout according to a step at respective steps in the clinical workflow. The display server 30 causes the medical diagnostic-imaging apparatus 10, the operating terminal 20, and a device connected to the network 40 to display the screen in a layout according to a step. For example, the display server 30 is implemented by a computer device, such as a server and a work station.

The clinical workflow is a flow including multiple steps in a medical workflow. For example, the clinical workflow may be a flow of a series of procedures, such as operation and catheter treatment, or may be a flow of a series of treatment from a first visit until an end of therapy. Moreover, steps are respective stages in the clinical workflow. For example, when the clinical workflow is a procedure such as catheter treatment, steps are contrast radiography of coronary artery, catheter penetration of a narrowed portion, and the like. When the clinical workflow is a flow of a series of treatment, steps are a first visit, diagnostic imaging, definite diagnosis, and the like. Moreover, the display server 30 may be one that displays a scree relating to any medical information, not limited to a screen relating to a procedure, such as operation and catheter treatment. For example, the display server 30 may be configured to display a screen relating to an electronic chart, a screen relating to a diagnostic imaging report, and a screen relating to an electrocardiogram.

The display server 30 causes the operating terminal 20 to display a screen having plural views in a layout determined for each step in the clinical workflow. The view is a display area that is associated with information available to be displayed. That is, the view is a display area in which specified medical information is displayed. The layout of a view of a screen displayed at each step in a clinical workflow is determined for each step. The layout may be determined for each facility such as hospital, may be determined for each department, may be determined for each healthcare worker, such as a doctor, and may be determined by an application.

There is a case in which a user that uses the clinical workflow changes the layout of a screen according to a condition of a patient. For example, the user sometimes adds a view according to a condition of a patient to a screen, or sometimes replaces the view. When the layout of the view is changed and the step in the clinical workflow transitions, the display server 30 determines whether to apply the layout change also to screens of steps after transition.

Figure 2:
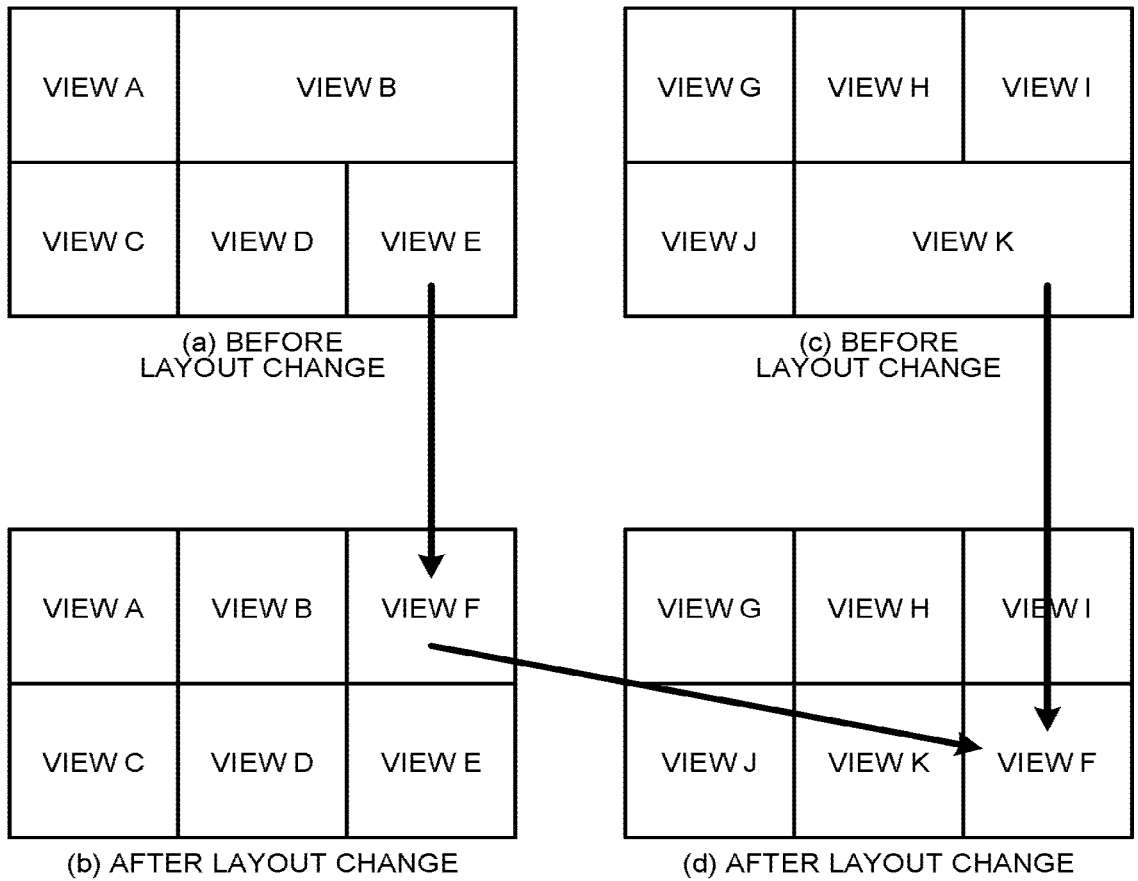
FIG. 2 is a diagram illustrating an example of layout change according to the first embodiment.

FIG. 2 is a diagram illustrating an example of a layout change according to the first embodiment. FIG. 2(*a*) illustrates a screen of a standard layout before a change at step A. FIG. 2(*b*) illustrates a screen after a layout change at step A. FIG. 2(*c*) illustrates a screen of a standard layout before a change at step B. FIG. 2(*d*) illustrates a screen after a layout change at step B.

As illustrated in FIG. 2, in the case of step A, the display server 30 displays a screen including view A, view B, view C, view D, and view E. Moreover, in the case of step B that is a step after step A, the display server 30 displays a screen including view G, view H, view I, view J, and view K, for example, as a standard screen.

In such a case, suppose that the user has performed a layout change of adding view F at step A as illustrated in FIG. 2(*b*). The display server 30 calculates a degree of importance of the changed view. That is, the display server 30 calculates the degree of importance of view F. Moreover, the display server 30 determines whether to apply a layout change based on the degree of importance. As illustrated in FIG. 2(*d*), when it is determined to apply the layout change, the display server 30 adds view F to the screen of step B.

Next, a configuration of the display server 30 according to the first embodiment will be explained.

As illustrated in FIG. 1, the display server 30 includes a network (NW) interface 310, an input interface 320, a display 330, a storage 340, and processing circuitry 350.

The NW interface 310 is connected to the processing circuitry 350, and controls transmission and communication of various kinds of data performed between itself and the respective devices connected through the network 40. For example, the NW interface 310 is implemented by a network card, a network adaptor, a network interface controller (NIC), or the like.

The input interface 320 is connected to the processing circuitry 350, and converts an input operation accepted from an operator (healthcare worker) into an electrical signal, to output to the processing circuitry 350. Specifically, the input interface 320 converts an input operation accepted from an operator into an electrical signal, to output to the processing circuitry 350. For example, the input interface 320 is implemented by a trackball, a switch button, a mouse, a keyboard, a touch pad with which an input operation is performed by touching an operating surface, a touch screen in which a display screen and a touch pad are integrated, a non-contact input circuit using an optical sensor, a sound input circuit, and the like. In the present specification, the input interface 320 is not limited to ones including a physical operating part, such as a mouse and a keyboard. For example, processing circuitry of an electrical signal that receives an electrical signal corresponding to an input operation from an external input device arranged separately from the device, and that outputs this electrical signal to the control circuit is also included in examples of the input interface 320.

The display 330 is connected to the processing circuitry 350, and displays various kinds of information and various kinds of image data output from the processing circuitry 350. For example, the display 330 is implemented by a liquid crystal display, a cathode ray tube (CRT) display, an organic EL display, a plasma display, a touch panel, and the like.

The storage 340 is connected to the processing circuitry 350, and stores various kinds of data. Moreover, the storage 340 stores various kinds of programs to implement various kinds of functions by being read and executed by the processing circuitry 350. For example, the storage 340 is implemented by a semiconductor memory device, such as a random access memory (RAM) and a flash memory, a hard disk, an optical disk, and the like.

For example, the storage 340 stores a user database 341, a step database 342, a view database 343, and a disease database 344.

Figure 3:
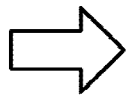
FIG. 3 is a diagram illustrating an example of a data configuration of a user database.

The user database 341 has information about users such as healthcare workers. FIG. 3 is a diagram illustrating an example of a data configuration of the user database 341. The user database 341 includes information of years of experience, department, profession, and the like. The years of experience is information indicating years of experience as a healthcare worker. The department is information indicating a department to which a user belongs. For example, the department is information indicating internal medicine, surgery, radiology, and the like. The profession is information indicating a profession of a user. For example, the profession is information indicating doctor, nurse, technician, and the like. Moreover, the user database 341 may include information other than these.

The step database 342 is a database of information that is suggested to be displayed to make a clinical decision at respective steps in the clinical workflow. FIG. 4 is a diagram illustrating an example of a data configuration of the step database 342. The step database 342 includes information such as display-suggested information of respective steps and a degree of importance. The display-suggested information is information suggested to be displayed to make decisions at the respective steps in the clinical workflow. The degree of importance is information indicating a degree of importance of display-suggested information associated therewith.

The view database 343 is a database of views. FIG. 5 is a diagram illustrating an example of a data configuration of the view database 343. The view database 343 includes displayable information of the respective views, information of a degree of importance, and the like. The displayable information is information that is displayed in each view. More specifically, the displayable information is medical information specified in each view. The degree of importance is information indicating a degree of importance of displayable information associated therewith.

Figures 6, 7:
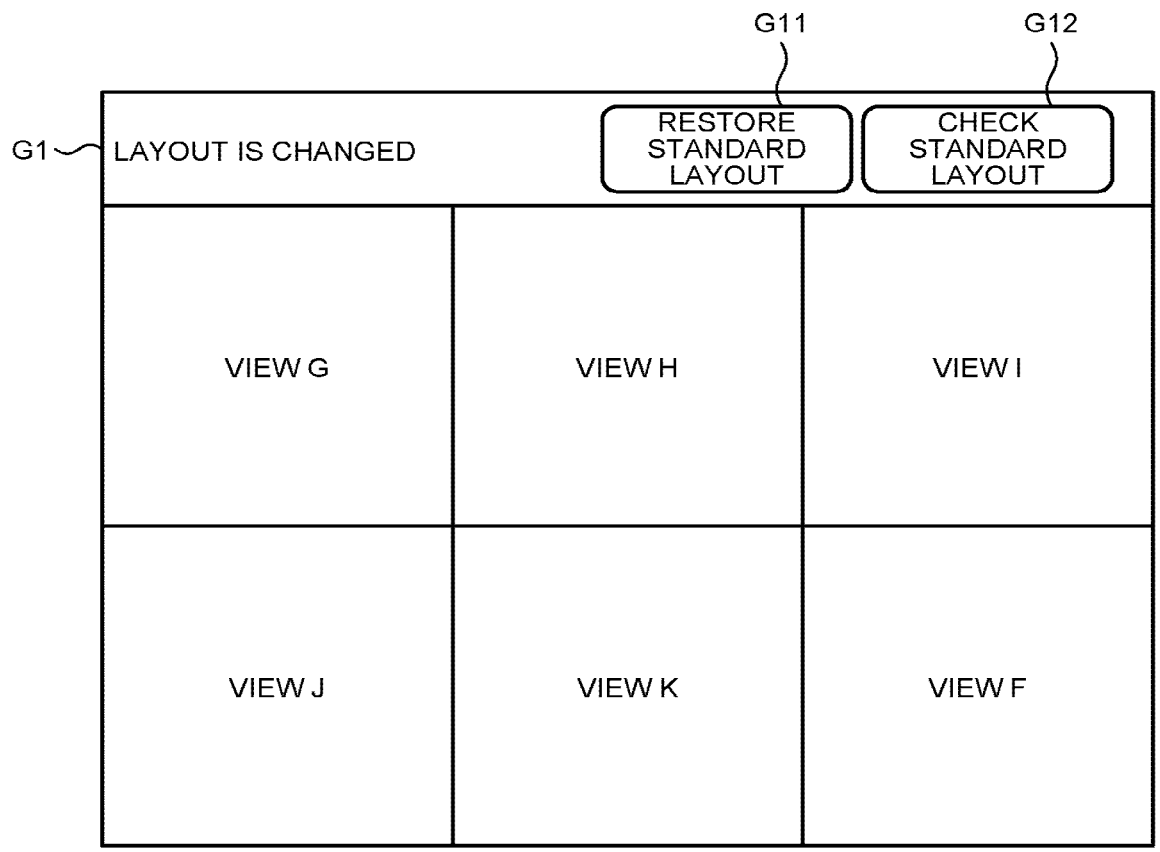
FIG. 6 is a diagram illustrating an example of a data configuration of a disease database.
FIG. 7 is a diagram illustrating an example of a second screen to which notification image is added.

The disease database 344 is a database relating to diseases. FIG. 6 is a diagram illustrating an example of a data configuration of the disease database 344. The disease database 344 includes monitoring information of respective diseases, information of a degree of importance, and the like. The monitoring information is information that is suggested to be monitored for the respective diseases. The degree of importance is information indicating a degree of importance of monitoring information associated therewith.

The processing circuitry 350 controls overall operation of the display server 30. The processing circuitry 350 includes, for example, a layout-change recording function 351, a step-transition detecting function 352, an importance calculating function 353, a determining function 354, a layout changing function 355, and a display control function 356. In the embodiment, the respective processing functions performed by the layout-change recording function 351, the step-transition detecting function 352, the importance calculating function 353, the determining function 354, the layout changing function 355, and the display control function 356 being components are stored in the storage 340 in a form of computer-executable program. The processing circuitry 350 is a processor that reads and executes the programs from the storage 340, to thereby implement the functions corresponding to the respective programs. In other words, the processing circuitry 350 that has read the respective programs are to have the respective functions indicated in the processing circuitry 350 in FIG. 1.

In FIG. 1, it is explained that the layout-change recording function 351, the step-transition detecting function 352, the importance calculating function 353, the determining function 354, the layout changing function 355, and the display control function 356 are implemented by a single unit of processor, but it may be configured such that plural independent processors are combined to constitute the processing circuitry 350, and the functions are implemented by the respective processors executing the programs. Moreover, in FIG. 1, it is explained that a single unit of storage, such as the storage 340, stores the programs corresponding to the respective processing functions, but it may be configured such that plural units of storages are arranged in a distributed manner, and the processing circuitry 350 reads out a corresponding program from an independent storage.

A term "processor" used in the above explanation signifies a circuit, such as a central processing unit (CPU), a graphical processing unit (GPU), an application specific integrated circuit (ASIC), a programmable logic device (for example, simple programmable logic device (SPLD), complex programmable logic device (CPLD)), and a field programmable gate array (FPGA). The processor implements a function by reading and executing a program stored in the storage 340.

Moreover, instead of storing a program in the storage 340, it may be configured to directly install a program in a circuit of the processor. In this case, the processor reads and executes the program installed in the circuit, to implement the function.

The layout-change recording function 351 records, when a layout of a display area is changed at a first step included in the clinical workflow, layout change information that indicates a changed content. The layout-change recording function 351 is one example of a recording unit. A first screen is a screen in which the layout is changed by a user. The layout change information includes information to identify a screen in which a layout is changed, and information to identify a changed view. Moreover, the layout change information may include a user code to identify a user that has changed the layout.

More specifically, the layout-change recording function 351 generates layout change information when it is detected that a layout has been changed by a user. The layout-change recording function 351 then stores the layout change information in the storage 340, and the like.

The step-transition detecting function 352 detects transition of step in the clinical workflow. More specifically, the step-transition detecting function 352 detects a transition condition of step that is determined for each step. The transition condition may be any kind. For example, the transition condition may be an operation to specify transition of step, may be detection by a sensor arranged on an instrument used for a procedure, may be an image recognition result of an image captured by a camera arranged in an operating room, or may be registration of specific information, such as of definite diagnosis.

The importance calculating function 353 calculates a degree of importance of a changed view that is indicated in the layout change information. The importance calculating function 353 is one example of a calculating unit. That is, the importance calculating function 353 calculates a degree of importance of the changed view based on a degree of importance of the display-suggested information that is suggested to be displayed at a second step after the first step corresponding to the first screen, and on a degree of importance of the displayable information of the changed view. The second step is a step in the clinical workflow provided after the first step corresponding to the first screen. That is, the second step may be a step following the first step, or may be a step after two or more transitions after the first step. Moreover, at the second step, the first screen is displayed.

Furthermore, the importance calculating function 353 acquires a degree of importance of one or more pieces of the display-suggested information associated with the second step from the step database 342. Furthermore, the importance calculating function 353 acquires a degree of importance of one or more pieces of the displayable information associated with the changed view from the view database 343. The importance calculating function 353 calculates a degree of importance of the changed view based on the degree of importance of the display-suggested information and the degree of importance of the displayable information of the changed view.

For example, the importance calculating function 353 multiplies the degrees of importance of the display-suggested information and of the displayable information indicating the same content. The importance calculating function 353 adds up the respective multiplied values indicating the same content. Thus, the importance calculating function 353 calculates the degree of importance of the changed view.

For example, in the step database 342 illustrated in FIG. 4 and the view database 343 illustrated in FIG. 5, the importance calculating function 353 multiplies information A of the display-suggested information and information A of the displayable information. Moreover, the importance calculating function 353 multiplies information B of the display-suggested information and information B of the displayable information. Furthermore, the importance calculating function 353 multiplies information C of the display-suggested information and information C of the displayable information. The importance calculating function 353 then calculates the degree of importance of the view by adding up the multiplied value of information A, the multiplied value of information B and the multiplied value of information C.

The view changed by the user is added because it is determined to be important by the user. Accordingly, the importance calculating function 353 may perform processing by which the degree of importance of a view changed by a user becomes high. For example, the importance calculating function 353 may add a specific value to the calculated degree of importance of the view, may multiply the calculated degree of importance of the view by a specific value, or may perform other processing.

The determining function 354 determines, when a layout of a display area is changed at the first step, whether to change a layout of a display area that has been set in advance for the second step that is any of steps after the first step based on the layout change information. The determining function 354 is one example of a determining unit. In other words, the determining function 354 determines whether to change a layout at the second step based on the degree of importance calculated by the importance calculating function 353 based on the layout change information.

For example, the determining function 354 determines to change the layout when the degree of importance of the change view indicated in the layout change information is higher than the degree of importance of the view included in the second screen. On the other hand, the determining function 354 determines not to change the layout when the degree of importance of the changed view indicated in the layout change information is lower than the degree of importance of the view included in the second screen. Not limited to a relative degree of importance, the determining function 354 may determine to change the layout when the degree of importance of the changed view indicated in the layout change information is higher than a threshold, or may determine by other methods.

The layout changing function 355 changes the layout at the second step based on a determination result of the determining function 354. The layout changing function 355 is one example of a changing unit. More specifically, the layout changing function 355 changes screen layout information indicating a layout of a screen to be displayed at each step in the clinical workflow. The screen layout information is information indicating a layout of a view included in a screen. For example, the screen layout information includes view identification information to identify a view included in a screen, position information indicating a position at which each view is displayed, and information indicating a size of each view.

For example, when addition of a view is indicated in the layout change information, the layout changing function 355 adds the view added in the layout change information to the second screen, or replaces the view of the second screen, based on the size of the second screen. More specifically, the layout changing function 355 determines whether the size of each view is equal to or larger than a threshold when a view identified by the view identification information included in the screen layout information and the changed view indicated in the layout change information are displayed. In other words, the layout changing function 355 determines whether an area of each view in the screen is equal to or larger than the threshold.

The layout changing function 355 adds a view indicated in the layout change information when the area of the view is equal to or larger than the threshold. That is, the layout changing function 355 adds the view changed by a user to the screen layout information indicating the layout of the second screen.

On the other hand, the layout changing function 355 adds the changed view indicated in the layout change information by replacing the views when the area of the view is smaller than the threshold. For example, the layout changing function 355 replaces the view having a low degree of importance out of views identified by the view identification information included in the screen layout information, with the changed view indicated in the layout change information. That is, the layout changing function 355 replaces views in the screen layout information indicating the layout of the second screen.

The display control function 356 displays a screen according to respective steps in the clinical workflow based on the screen layout information indicating a layout of a view associated with the displayable information of a subject to be displayed. For example, the display control function 356 displays the screen in which the layout has been changed by the layout changing function 355 on the operating terminal 20 and the like. The display control function 356 may display the screen in which the layout has been changed by the layout changing function 355, on not limited to the operating terminal 20, but also on a display of the medical diagnostic-imaging apparatus 10 or on a display of other devices installed in a hospital.

More specifically, the display control function 356 displays the first screen based on the screen layout information at the first step. Moreover, the display control function 356 displays the second screen based on the screen layout information at the second step.

Furthermore, the display control function 356 displays the second screen to which a notification image G1 notifying that the layout has been changed is added, when displaying the second screen in which the layout has been changed by the layout changing function 355. The display control function 356 is one example of a display control unit. FIG. 7 is a diagram illustrating an example of the second screen to which the notification image G1 is added. As illustrated in FIG. 7, the notification image G1 notifies that the view of the second screen has been changed. Moreover, the notification image G1 includes a restore button G11 and a check button G12.

The restore button G11 is a button to accept an operation to restore the second screen of the standard layout in which the view is not changed. The display control function 356 displays the second screen in the standard layout when the restore button G11 is pressed. Therefore, the user can restore the standard layout easily when an unnecessary layout change has been performed.

The check button G12 is a button to temporarily display the second screen in the standard layout in which the view is not changed. The display control function 356 temporarily displays the second screen in the standard layout when the restore button G11 is pressed. Therefore, the user can judge which one of the second screen in which the layout is changed or the second screen in the standard layout is appropriate screen.

Next, the respective processing performed by the display server 30 will be explained.

Figure 8:
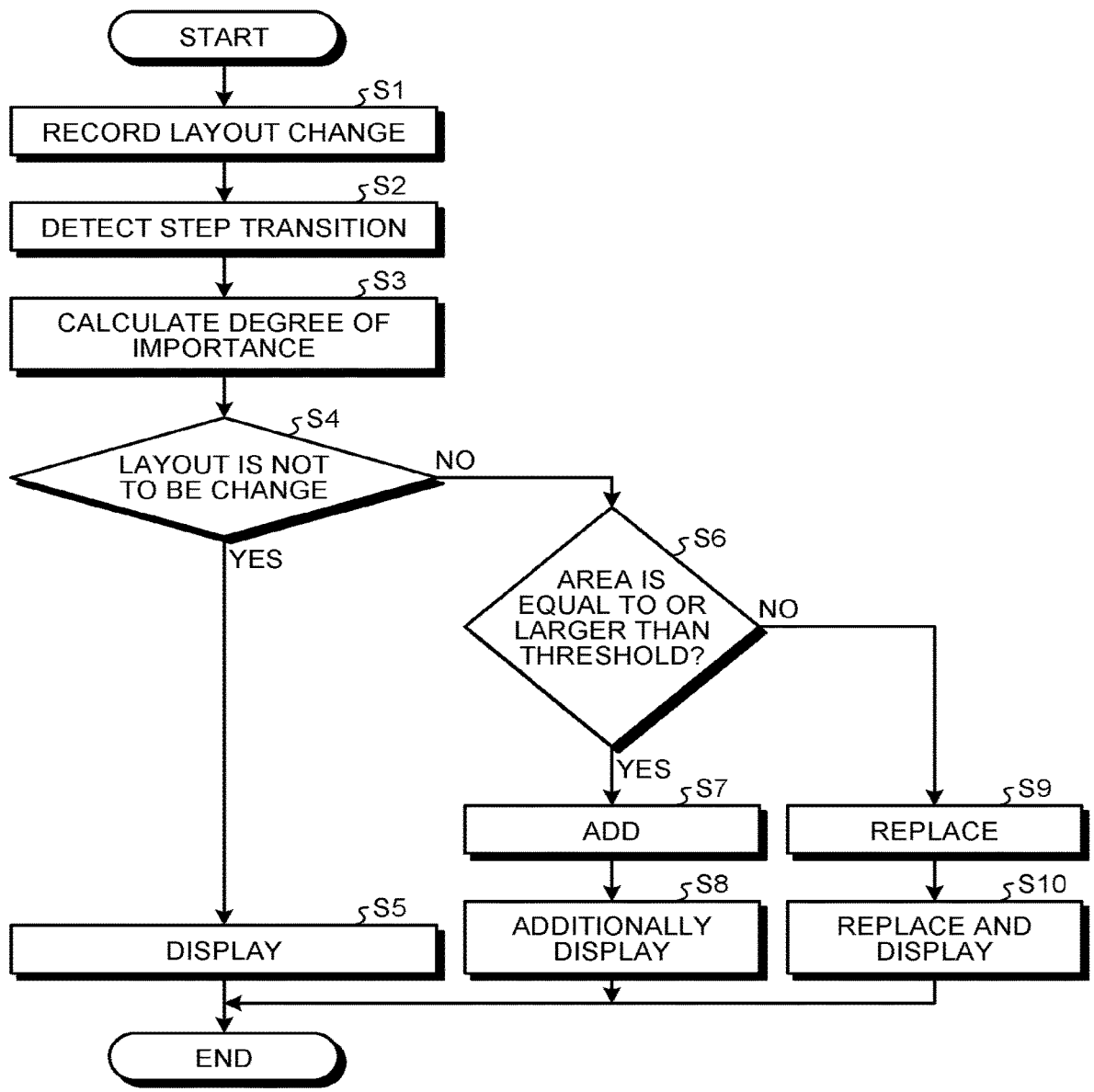
FIG. 8 is a flowchart illustrating an example of image display processing that is performed by a display server according to the first embodiment.

FIG. 8 is a flowchart illustrating an example of screen display processing that is performed by the display server 30 according to the first embodiment.

The layout-change recording function 351 records layout change information indicating a changed content when it is detected that a layout of a view included in a screen has been changed in a clinical workflow (step S1).

The step-transition detecting function 352 detects transition of steps in the clinical workflow (step S2).

The importance calculating function 353 calculates the degree of importance of the changed view (step S3).

The determining function 354 determines whether to change the layout of the view of the screen to be displayed at a step after transition based on the calculated degree of importance (step S4).

When the layout of the view of the screen is not to be changed (step S4: YES), the display control function 356 displays the screen of the standard layout on the operating terminal 20 and the like (step S5).

When the layout of the view of the screen is to be changed (step S4: NO), the layout changing function 355 determines whether an area of the view of the screen is equal to or larger than a threshold (step S6).

When the area of the view of the screen is equal to or larger than threshold (step S6: YES), the layout changing function 355 adds the changed view to the screen (step S7). That is, the layout changing function 355 adds the view changed by the user to the screen layout information indicating the layout of the screen to be displayed at a step after transition.

The display control function 356 displays the screen in the layout in which the view is added on the operating terminal 20 and the like (step S8).

When the area of the view of the screen is smaller than the threshold (step S6: NO), the layout changing function 355 adds the changed view to the screen by replacing them (step S9). That is, the layout changing function 355 replaces the view in the screen layout information indicating the layout of the screen to be displayed at a step after transition.

The display control function 356 displays the screen of the layout in which the view is replaced on the operating terminal 20 and the like (step S10).

Thus, the display server 30 ends the image display processing.

As described above, the display server 30 according to the first embodiment records the layout change information indicating the changed content in the layout when an operation of adding a view to the first screen to be displayed at a step in the clinical workflow, or replacing views is accepted. Moreover, the display server 30 determines whether to change the layout of the second screen according to the second step after the first step corresponding to the first screen, based on the layout change information. The display server 30 changes the layout of the second screen based on a result of determination. Thus, the display server 30 displays the second screen in which the change in the layout is reflected on the operating terminal 20 and the like at the second step transitioned from the first step. Therefore, the display server 30 can reduce trouble in layout change.

First Modification

It has been explained that the importance calculating function 353 according to the first embodiment calculates a degree of importance of view based on a degree of importance of display-suggested information and a degree of importance of display subject information. However, the importance calculating function 353 may calculate the degree of importance of a view based on a degree of importance of the display-suggested information, a degree of importance of the display subject information, and a degree of importance of information that is suggested to be displayed for each disease.

When a disease affecting a patient is determined, or when a medical condition is determined, important information varies depending on a disease affecting the patient. That is, monitoring information to be observed varies depending on a disease affecting a patient. The monitoring information is information that is acquired by measuring a patient. For example, the monitoring information is information of body temperature, a blood flow rate, a heart rate, an amount of movement of a specific portion of the heart, a degree of oxygen saturation, and the like.

The importance calculating function 353 calculates the degree of importance of the view based on a degree of importance of the display-suggested information, a degree of importance of the display subject information, and a degree of importance of the monitoring information that is suggested to be displayed for each disease. More specifically, the importance calculating function 353 acquires a degree of importance of one or more pieces of the display-suggested information associated with the second step from the step database 342. Moreover, the importance calculating function 353 acquires a degree of importance of one or more pieces of the display subject information associated with the changed view from the view database 343. Furthermore, the importance calculating function 353 acquires a degree of importance of monitoring information of a disease that is suspected that the patient is affected or a disease definitely diagnosed, from the disease database 344. The importance calculating function 353 calculates the degree of importance of the changed view based on the degree of importance of the display-suggested information, the degree of importance of the display subject information, and the degree of importance of the monitoring information that is suggested to be display for each disease.

For example, the importance calculating function 353 multiplies the degrees of importance of the display-suggested information, the display subject information, and the monitoring information that indicate the same content. The importance calculating function 353 then adds up respective multiplied values indicating the same content. Thus, the importance calculating function 353 calculates the degree of importance of the view. Moreover, when there are plural diseases that are suspected that the patient is affected, the importance calculating function 353 may assign weights based on the possibility of being affected by the disease.

For example, when the possibility of being affected by disease A is 40 percent, the possibility of being affected by disease B is 30 percent, and the possibility of being affected by disease C is 30 percent, the degree of importance of the monitoring information of disease A is multiplied by 0.4, the degree of importance of the monitoring information of disease B is multiplied by 0.3, and the degree of importance of the monitoring information of disease C is multiplied by 0.3. The importance calculating function 353 multiplies the degrees of importance subjected to weighting of the display-suggested information, the display subject information, and the monitoring information indicating the same content. The importance calculating function 353 then adds up the respective multiplied values indicating the same content. Thus, the importance calculating function 353 calculates the degree of importance of a view assigned a weight for each disease.

As described above, the display server 30 according to the first modification calculates a degree of importance of a view based on a degree of importance of the display-suggested information, a degree of importance of the display subject information, and a degree of importance of the monitoring information that is suggested to be displayed for each disease. Therefore, the display server 30 can determine whether to add changed view to the second screen according to a disease affecting a patient.

Second Modification

When plural users respectively use the clinical workflow, the importance calculating function 353 may increase or decrease a degree of importance of a view depending on a user.

For example, for a technician that operates the medical diagnostic-imaging apparatus 10, even a view added by a doctor in charge has a low priority to see when it is about information not relating to diagnostic imaging. Moreover, because a doctor in charge should be aware of all information relating to a patient, the doctor should see a view added by a technician that operates the medical diagnostic-imaging apparatus 10 also. Accordingly, the importance calculating function 353 does not change the degree of importance of a view added by a doctor in charge when a technician sees the screen. On the other hand, the importance calculating function 353 increases the degree of importance of a view added by a technician when a doctor in charge sees the screen.

Alternatively, the importance calculating function 353 may increase the degree of importance when the user that has added a view has many years of experience, or may increase the degree of importance when the job position of the user that has added a view is high.

More specifically, the importance calculating function 353 increases or decreases the degree of importance of a view based on the user database 341, a user code indicating a user that has changed a layout included in the layout change information, a user code indicating a user that is using the clinical workflow, and an increase/decrease condition that is a condition to increase or decrease the degree of importance of a view.

The importance calculating function 353 changes the degree of importance of a view according to a first user that has changed the layout at the first step. For example, the importance calculating function 353 increases the degree of importance of a view when a user that has added a view has many years of experience, or the job position of the user is high.

The importance calculating function 353 changes the degree of importance of a view according to the first user and a second user that displays a layout at the second step. that is, the importance calculating function 353 changes the degree of importance of a view according to a relationship between the first user and the second user. For example, the importance calculating function 353 increases the degree of importance of an added view when the job position of a user that displays the second screen is lower than the job position of a user that has added the view.

As described above, the display server 30 according to the second modification adjusts the degree of importance of a view according to a user that has added or replaced a view of the first screen and a user that sees the second screen. Therefore, the display server 30 can display the second screen according to a user.

Second Embodiment

A display server 30*a* according to a second embodiment estimates a reason why a layout of a view of a screen is changed in a clinical workflow. The display server 30*a* decreases the degree of importance when the reason of changing the layout is resolved.

Figure 9:
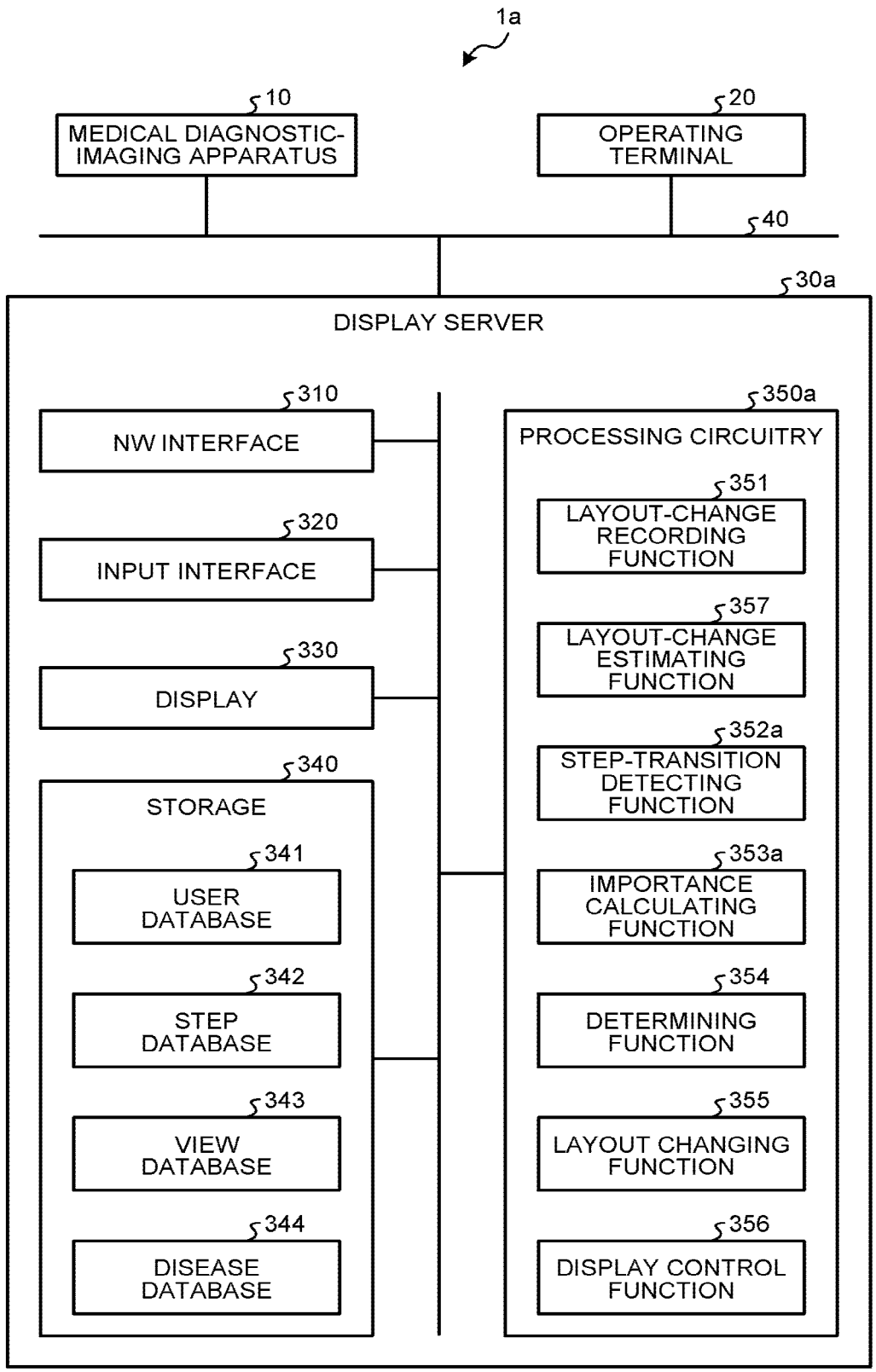
FIG. 9 is a block diagram illustrating an example of a configuration of a medical information-display system according to a second embodiment.

FIG. 9 is a block diagram illustrating an example of a configuration of a medical information-display system 1*a* according to the second embodiment. A processing circuitry 350*a* of the display server 30*a* includes a layout-change estimating function 357.

The layout-change estimating function 357 estimates a reason for which a layout of a view of a screen according to each step in the clinical workflow has been changed, and a resolution condition corresponding to the reason for change. The layout-change estimating function 357 is one example of an estimating unit. For example, the layout-change estimating function 357 estimates a reason for change based on a degree of importance of the view database 343. More specifically, the layout-change estimating function 357 estimates that the layout has been changed to see displayable information having the highest degree of importance out of changed views indicated by the layout change information.

For example, suppose that in a fluoroscopic view associated with the displayable information relating to an image of a patient fluoroscopically seen by X-rays, the degree of importance of blood stream information indicating stream in a blood vessel is 0.4, the degree of importance of angiostenosis information indicating narrowing of a blood vessel is 0.3, the degree of importance of position shape information indicating a shape of a position of a catheter is 0.3, and the degree of importance of exposure information indicating a radiation exposure level is 0. In this case, when a fluoroscopic view is added to a screen, the layout-change estimating function 357 determines that it is added to see the blood stream information.

Furthermore, the layout-change estimating function 357 estimates a detailed reason why displayable information having the highest degree of importance is desired to be seen. For example, the layout-change estimating function 357 compares a detailed reason set for each displayable information having the highest degree of importance, and a conformity condition indicating whether it corresponds to the detailed reason. The conformity condition is a condition of a patient input to an electronic chart, a condition detected by a sensor attached to a medical device, and the like. When determining that the conformity condition is satisfied, the layout-change estimating function 357 estimates that it is the applicable detailed reason.

For example, the layout-change estimating function 357 estimates that a view is added to see the blood stream information based on the degree of importance of the view database 343. Moreover, suppose that a detailed reason indicating malformation of a blood vessel is set to the blood stream information, and input to an electronic chart or a moving speed of a catheter is set as a conformity condition. In this case, the layout-change estimating function 357 estimates the detailed reason based on the input to the electronic chart or the moving speed of a catheter.

Alternatively, the layout-change estimating function 357 estimates that a view is added to see information indicating an exposure level based on the degree of importance of the view database 343. Suppose that a detailed reason indicating an exposure level is set to the information indicating an exposure level, and an exposure level equal to or higher than a threshold is set as a conformity condition. In this case, the layout-change estimating function 357 estimates the detailed reason based on whether it is an exposure level equal to or higher than the threshold.

Furthermore, the layout-change estimating function 357 estimates whether the resolution condition set for each detailed reason is satisfied. For example, when the detailed reason is malformation of a blood vessel, the layout-change estimating function 357 estimates that the resolution condition is satisfied when a catheter passes through a portion of the malformation of the blood vessel. For example, when the detailed reason is an exposure level, the layout-change estimating function 357 estimates that the resolution condition is satisfied when irradiation of an X-ray is ended.

A step-transition detecting function 352*a* detects that a step in the clinical workflow has transitioned. Moreover, the step-transition detecting function 352*a* detects that the resolution condition estimated by the layout-change estimating function 357 is satisfied as transition of a step. For example, the step-transition detecting function 352*a* detects that a catheter has passed through a portion of malformation of a blood vessel as transition of a step. Moreover, the step-transition detecting function 352*a* detects an end of irradiation of an X-ray as transition of a step.

When a resolution condition corresponding to a reason for change of an added view is satisfied, the display server 30*a* is not necessary to display the view added on the second screen. Accordingly, an importance calculating function 353*a* reduces the degree of importance of the view when the resolution condition corresponding to the reason for change is satisfied.

More specifically, when the step-transition detecting function 352*a* detects that a resolution condition is satisfied, the importance calculating function 353*a* reduces a calculated degree of importance of the view. For example, the importance calculating function 353*a* subtracts a specific value from the calculated degree of importance of the view. Thus, the added view has a reduced degree of importance of view and, therefore, is not to be displayed on the second screen at the second step. Therefore, the view, the reason for addition of which is resolved is not to be displayed.

Figure 10:
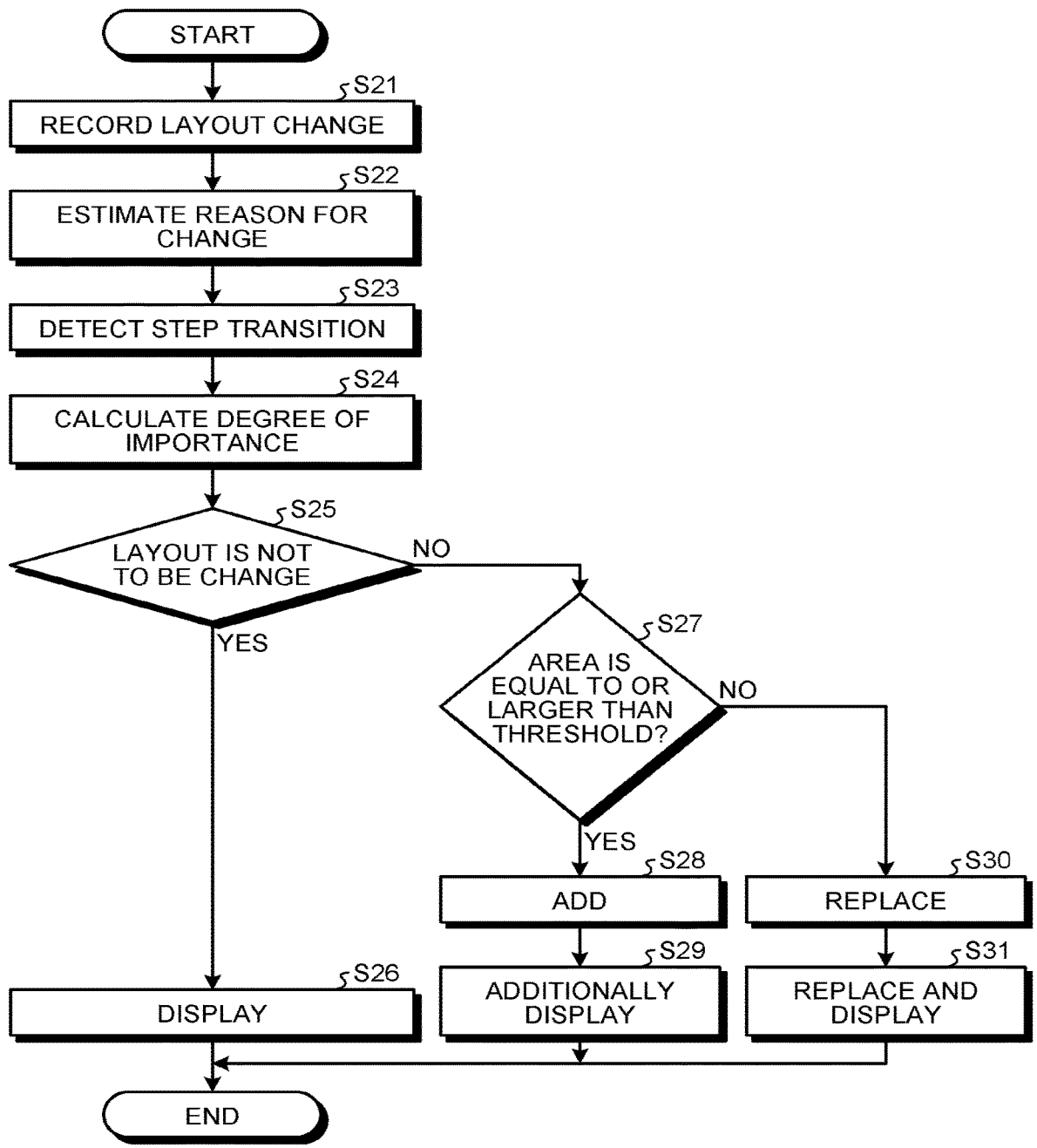
FIG. 10 is a flowchart illustrating an example of image display processing that is performed by a display server according to the second embodiment.

FIG. 10 is a flowchart illustrating an example of image display processing that is performed by the display server 30a according to the second embodiment.

The layout-change recording function 351 records, when a change in layout of a view included in a screen in the clinical workflow is detected, the changed screen and the changed view (step S21).

The layout-change estimating function 357 estimates a reason for change, a detailed reason of the reason for change, and a resolution condition for the detailed reason (step S22).

The step-transition detecting function 352a detects that the resolution condition for the detailed reason is satisfied as step transition (step S23).

The importance calculating function 353a calculates a degree of importance of the changed view, and reduces the calculated degree of importance of the view (step S24).

At step S25 to step S31, processing similar to those at step S4 to step S10 of the image display processing according to the first embodiment illustrated in FIG. 8 is performed.

As described above, the display server 30a according to the second embodiment estimates a reason for which a layout is changed, and a resolution condition corresponding to the reason for change. The display server 30a reduces a degree of importance of a changed view when the resolution condition for the reason for change is satisfied. Therefore, the display server 30a can suppress display of a view that is no longer necessary.

Moreover, in the first embodiment, the first modification, the second modification, and the second embodiment, it has been explained that the display servers 30, 30a include the layout-change recording function 351, the step-transition detecting functions 352, 352a, the importance calculating function 353, 353a, the determining function 354, the layout changing function 355, the display control function 356, and the layout-change estimating function 357. But all of or a part of functions of the layout-change recording function 351, the step-transition detecting functions 352, 352a, the importance calculating functions 353, 353a, the determining function 354, the layout changing function 355, the display control function 356, and the layout-change estimating function 357 may be included in the operating terminal 20, or may be included in the medical diagnostic-imaging apparatus 10.

According to at least one of the embodiments and the like explained above, trouble in layout change can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
processing circuitry configured to
record, when there is a layout change of a display area on a first screen of a display corresponding to a first step included in a clinical workflow, layout change information that indicates a changed content,
detect a transition from the first step to a second step, the second step being a step subsequent to the first step,
calculate a third degree of importance of the display area indicated in the layout change information at the second step, based on a first degree of importance of each piece of display-suggested information that is suggested to be displayed at each of a plurality of steps included in the clinical workflow, and a second degree of importance of each piece of displayable information in the display area after the layout change,
determine whether or not to change a layout of a display area on a second screen of the display corresponding to the second step, based on the calculated third degree of importance,
change the layout of the second screen corresponding to the second step based on a result of the determination, and
display the second screen on the display.

2. The medical information processing apparatus according to claim 1, wherein
the processing circuitry is further configured to calculate the third degree of importance of the display area based on the first degree of importance, the second degree of importance, and a fourth degree of importance of monitoring information that is suggested to be displayed for each disease.

3. The medical information processing apparatus according to claim 1, wherein the processing circuitry is further configured to estimate a reason for change for which the layout has been changed, and a resolution condition corresponding to the reason for the change.

4. The medical information processing apparatus according to claim 1, wherein the processing circuitry is further configured to perform, when the layout change information indicates addition of the display area, any one of an addition of the display area that is added in the layout change information, and a replacement of the display area based on a size of the display area.

5. The medical information processing apparatus according to claim 1, wherein the processing circuitry is further configured to change the third degree of importance of the display area according to a first user that has changed the layout at the first step.

6. The medical information processing apparatus according to claim 5, wherein the processing circuitry is further configured to change the third degree of importance of the display area according to the first user and a second user that displays the layout at the second step.

7. The medical information processing apparatus according to claim 1, wherein the processing circuitry is further configured to display a notification image to notify that the layout has been changed.

8. A medical information processing method, comprising:
recording, when there is a layout change of a display area on a first screen of a display corresponding to a first step included in a clinical workflow, layout change information that indicates a changed content,
detecting a transition from the first step to a second step, the second step being a step subsequent to the first step,
calculating a third degree of importance of the display area indicated in the layout change information at the second step, based on a first degree of importance of each piece of display-suggested information that is suggested to be displayed at each of a plurality of steps included in the clinical workflow, and a second degree of importance of each piece of displayable information in the display area after the layout change, determining whether or not to change a layout of a display area on a second screen of the display corresponding to the second step, based on the calculated third degree of importance, changing the layout of the second screen corresponding to the second step based on a result of determination, and displaying the second screen on the display.

9. The medical information processing apparatus of claim 1, wherein the processing circuitry is configured to record the layout change information in an electronic memory when detecting the layout change, which is initiated by an operator.

10. The medical information processing apparatus of claim 1, wherein, in calculating the third degree of importance, the processing circuitry is configured to extract the degree of importance information from an electronic memory.

* * * * *